(12) United States Patent
Torabi

(10) Patent No.: US 12,094,205 B2
(45) Date of Patent: Sep. 17, 2024

(54) USER SWITCHING DETECTION DURING ROBOTIC SURGERIES USING DEEP LEARNING

(71) Applicant: Verb Surgical Inc., Santa Clara, CA (US)

(72) Inventor: Meysam Torabi, Union City, CA (US)

(73) Assignee: Verb Surgical Inc., Santa Clara, CA (US)

(*) Notice: Subject to any disclaimer, the term of this patent is extended or adjusted under 35 U.S.C. 154(b) by 0 days.

(21) Appl. No.: 17/960,680

(22) Filed: Oct. 5, 2022

(65) Prior Publication Data

US 2023/0036019 A1 Feb. 2, 2023

Related U.S. Application Data

(63) Continuation of application No. 17/017,540, filed on Sep. 10, 2020, now Pat. No. 11,488,382.

(51) Int. Cl.
*G06V 20/00* (2022.01)
*A61B 34/30* (2016.01)
(Continued)

(52) U.S. Cl.
CPC .............. *G06V 20/41* (2022.01); *A61B 34/30* (2016.02); *G06F 18/214* (2023.01); *G06F 18/24* (2023.01);
(Continued)

(58) Field of Classification Search
CPC ........ G06V 20/41; G06V 10/40; G06V 20/46; G06V 20/36; G06V 10/774; G06V 10/82;
(Continued)

(56) References Cited

U.S. PATENT DOCUMENTS 10,679,046 B1 6/2020 Black et al.
2016/0350610 A1* 12/2016 Yoo .......................... G06T 7/73
(Continued)

FOREIGN PATENT DOCUMENTS

EP 2966371 1/2016

OTHER PUBLICATIONS

He et al, Deep Residual Learning for Image Recognition, arXiv:1512.023385v1 (Year: Dec. 10, 2015).*
(Continued)

*Primary Examiner* — Ping Y Hsieh
*Assistant Examiner* — Xiao Liu
(74) *Attorney, Agent, or Firm* — Aikin & Gallant, LLP

(57) ABSTRACT

Various user-presence/absence detection techniques based on deep learning are provided. These user-presence/absence detection techniques can include building/training a deep-learning model including a user-presence/absence classifier based on training images of a user-seating area of a surgeon console under various clinically-relevant conditions. The trained user-presence/absence classifier can then be used during teleoperation/surgical procedures to monitor/track users in the user-seating area of the surgeon console, and continuously classify captured real-time video images of the user-seating area into either a user-presence classification or a user-absence classification. In some embodiments, the user-presence/absence classifier can be used to detect a user-switching event at the surgeon console when a second user is detected to have entered the user-seating area after a first user is detected to have exited the user-seating area. If the second user is identified as a new user, this can trigger a recalibration procedure to recalibrate surgeon-console settings for the new user.

20 Claims, 10 Drawing Sheets

(51) Int. Cl.
- *G06F 18/214* (2023.01)
- *G06F 18/24* (2023.01)
- *G06N 3/04* (2023.01)
- *G06N 3/08* (2023.01)
- *G06T 3/4046* (2024.01)
- *G06T 3/60* (2006.01)
- *G06T 7/11* (2017.01)
- *G06T 7/70* (2017.01)
- *G06V 10/40* (2022.01)
- *G06V 20/40* (2022.01)

(52) U.S. Cl.
CPC ............... *G06N 3/04* (2013.01); *G06N 3/08* (2013.01); *G06T 3/4046* (2013.01); *G06T 3/60* (2013.01); *G06T 7/11* (2017.01); *G06T 7/70* (2017.01); *G06V 10/40* (2022.01); *G06V 20/46* (2022.01); *A61B 2034/301* (2016.02); *G06T 2207/10016* (2013.01); *G06T 2207/20081* (2013.01); *G06T 2207/20084* (2013.01); *G06T 2207/20132* (2013.01); *G06T 2207/30196* (2013.01)

(58) Field of Classification Search
CPC . A61B 34/30; A61B 2034/301; G06F 18/214; G06F 18/24; G06N 3/04; G06N 3/08; G06N 3/0464; G06T 3/4046; G06T 3/60; G06T 7/11; G06T 7/70; G06T 2207/10016; G06T 2207/20081; G06T 2207/20084; G06T 2207/20132; G06T 2207/30196
See application file for complete search history.

(56) References Cited

U.S. PATENT DOCUMENTS

| | | | |
|---|---|---|---|
| 2018/0092706 A1* | 4/2018 | Anderson | A61B 34/74 |
| 2018/0373980 A1 | 12/2018 | Huval | |
| 2019/0258866 A1* | 8/2019 | Khadloya | G06V 40/103 |
| 2019/0294924 A1 | 9/2019 | Gould et al. | |
| 2020/0054306 A1 | 2/2020 | Mehanian et al. | |

OTHER PUBLICATIONS

International Search Report and Written Opinion for International Application No. PCT/US2020/051159 mailed Jun. 4, 2021, 18 pages.

Cerutti, Gianmarco, et al., "Convolutional Neural Networks on Embedded Platform for People Presence Detection in Low Resolution Thermal Images," ICASSP 2019—2019 IEEE International Conference on Acoustics, Speech and Signal Processing, May 12, 2019, pp. 7610-7614.

D'Innocente, Antonio, et al., "Bridging Between Computer and Robot Vision Through Data Augmentation: A Case Study on Object Recognition," ICIAP: International Conference on Image Analysis and Processing, Sep. 9-13, 2013 10 pages.

Han, Changehee, et al., Learning more with less: Conditional PGGAN-based data augmentation for brain metastases detection using highly-rough annotation on MR images, CIKM'19, Nov. 3-7, pp. 119-127 (Year: 2019).

\* cited by examiner

USER SWITCHING DETECTION DURING ROBOTIC SURGERIES USING DEEP LEARNING

PRIORITY CLAIM AND RELATED PATENT APPLICATIONS

This patent application is a continuation of, and hereby claims the benefit of priority under 35 U.S.C. § 120 to co-pending U.S. patent application Ser. No. 17/017,540, filed on Sep. 10, 2020, entitled, "USER PRESENCE/ABSENCE RECOGNITION DURING ROBOTIC SURGERIES USING DEEP LEARNING," by inventor Meysam Torabi. The above-listed application is hereby incorporated by reference as a part of this patent document.

TECHNICAL FIELD

The present disclosure generally relates to robotic surgical systems, and more specifically to systems, devices and techniques for automatically recognizing users/surgeons' presence at or absence from surgeon consoles during robotic surgeries.

BACKGROUND

Endoscopic surgery involves looking into a patient's body and performing surgery inside the patient's body using endoscopes and other surgical tools. For example, laparoscopic surgery can use a laparoscope to access and view an abdominal cavity. Endoscopic surgery can be performed using manual tools and/or a robotic surgical system having robotically-assisted tools.

A robotic surgical system may be remotely operated by a surgeon to command a robotically-assisted surgical tool located at an operating table. Such operation of a robotically-assisted tool remotely controlled by a surgeon may be commonly referred to as teleoperation. For example, the surgeon may use a computer console located in the operating room, or it may be located in a different city, to command a robot to manipulate the surgical tool mounted on the operating table. The robotically-assisted tools can include an endoscope mounted on a robotic arm. Accordingly, the surgical robotic system may be used by the remote surgeon to perform an endoscopic surgery.

The surgeon console of the robotic surgical system often includes an eye tracking mechanism configured to track the gaze of a user/surgeon during a surgical procedure. For a given surgeon using the surgeon console during a new surgical procedure, the eye tracking mechanism needs to be calibrated or otherwise configured for the surgeon before starting the new surgical procedure. During the subsequent surgical procedure, the surgeon may need to leave the console for a number of reasons, such as to get help with the procedure. After the surgeon has left the console, it is possible that a new surgeon steps in and takes over the surgical procedure. When this user-swap event occurs, the robotic surgical system needs to ensure that the eye tracking settings are recalibrated or reconfigured for the new surgeon, because different users typically have different eye tracking settings. However, existing robotic surgical systems do not include mechanisms to detect such user-swap events during a surgical procedure. As a result, existing robotic surgical systems would continue to use the eye tracking settings of the previous surgeon on the new surgeon, which can lead to inaccurate eye-tracking control signals that would further lead to unsafe/unintended robotic arm or tool motions.

SUMMARY

Disclosed are various user-presence/absence recognition techniques based on image processing and deep learning. More specifically, various user-presence/absence recognition techniques include building/training a convolutional neural network (CNN)-based image recognition model including a user-presence/absence classifier based on training images collected from the user-seating area of a surgeon console within a robotic surgical system under various clinically-relevant conditions/cases. The trained user-presence/absence classifier can then be used during teleoperation/surgical procedures to monitor/track users in the user-seating area of the surgeon console, and continuously classify the real-time video images of the user-seating area as either a user-presence state or a user-absence state.

In some embodiments, the disclosed user-presence/absence recognition techniques can be used to detect a user-switching event at the surgeon console when a second user is detected to have entered the user-seating area after a first user is detected to have exited the user-seating area. The detection of the user-switching event allows for prompting the second user in the user-seating area to identify him/herself as either the same user as the first user or a different user. If the second user is identified as a new user, the disclosed user-presence/absence recognition techniques can trigger a recalibration procedure for the new user of user-console settings, including but are not limited to: user gaze-tracking settings; user UID-control settings; and user seat settings (e.g., the armrest settings).

In one aspect, a system for detecting user switching events at a surgeon console in a robotic surgical system is disclosed. During operation, this system can begin by receiving a first sequence of video images capturing a user seating area of the surgeon console. Next, the system processes the first sequence of video images to detect a first user exiting the user seating area after detecting the first user being present at the user seating area. The system further receives a second sequence of video images capturing the user seating area. The system then processes the second sequence of video images to detect a second user entering the user seating area. Next, the system verifies whether the second user is the same as the first user. The system subsequently determines that a user switching event has occurred at the surgeon console in response to verifying that the second user is not the same as the first user.

In some embodiments, the system processes the first sequence of video images to detect the first user exiting the user seating area by applying a user-presence/absence classifier to the first sequence of video images to generate a corresponding sequence of user-presence/user-absence classifications. Note that the user-presence/absence classifier is configured to output a binary classification for each input image as either a user-presence classification or a user-absence classification. The system then detects the first user exiting the user seating area when the generated user-presence/user-absence classifications transition from continuous user-presence classifications to user-absence classifications.

In some embodiments, the system processes the second sequence of video images to detect the second user entering the user seating area by applying the user-presence/absence classifier to the second sequence of video images to generate a corresponding sequence of user-presence/user-absence classifications. The system then detects the second user entering the user seating area when the generated user-presence/user-absence classifications transition from continuous user-absence classifications to user-presence classifications.

In some embodiments, the system verifies whether the second user is the same as the first user by first generating a dialog window on a monitor within the surgeon console prompting the second user to respond whether he/she is the same user as the first user. Next, the system receives a response from the second user through the dialog window. The system then determines whether the second user is the same as the first user based on the received response.

In some embodiments, to avoiding false positives, the system generates the dialog window only after a minimum number of consecutive user-presence classifications have been generated by the user-presence/absence classifier following the continuous user-absence classifications.

In some embodiments, after determining that a user switching event has occurred, the system further determines the identity of the second user. The system subsequently launches a surgeon-console recalibration procedure to recalibrate a set of settings of the surgeon console for the identified second user.

In some embodiments, the set of settings of the surgeon console includes one or more of: (1) user gaze-tracking settings; (2) user interface device (UID)-control settings; and (3) user seat settings.

In some embodiments, in response to verifying that the second user is the same as the first user, the system maintains the set of settings of the surgeon console for the first user.

In some embodiments, the user-presence/absence classifier includes a convolutional neural network (CNN) model that further comprises a stack of feature-extraction layers having a first set of parameters, which is followed by a fully-connected layer having a second set of parameters, which is further followed by a final output layer that outputs the user-presence/user-absence classifications.

In some embodiments, prior to detecting the user switching event, the system trains the user-presence/absence classifier by: (1) receiving a set of training images of the user seating area, wherein each training image in the set of training images is either labeled with a user-presence label or a user-absence label; (2) for each labeled training image in the set of training images, using the stack of feature-extraction layers of the CNN model to extract a set of two-dimensional (2D) feature maps of the labeled training image while freezing the first set of parameters; (3) training the second set of parameters of the fully-connected layer of the CNN model based at least on the sets of extracted 2D feature maps extracted from the set of training images and the corresponding set of user-presence/user-absence labels to obtain a trained fully-connected layer; and (4) freezing both the first set of parameters and the trained second set of parameters in the CNN model to obtain the trained user-presence/absence classifier.

In some embodiments, the final output layer includes a binary Softmax layer.

In another aspect, an apparatus is disclosed. This apparatus includes one or more processors and a memory coupled to the one or more processors. The memory of the apparatus stores instructions that, when executed by the one or more processors, cause the apparatus to: receive a first sequence of video images capturing a user seating area of the surgeon console; process the first sequence of video images to detect a first user exiting the user seating area after detecting the first user being present at the user seating area; receive a second sequence of video images capturing the user seating area; process the second sequence of video images to detect a second user entering the user seating area; verify whether the second user is the same as the first user; and determine that a user switching event has occurred at the surgeon console in response to verifying that the second user is not the same as the first user.

In yet another aspect, a robotic surgical system is disclosed. This robotic surgical system can include: a surgeon console including a user seating area and a display device; and a computer at the surgeon console configured to detect user a user switching event at the surgeon console by: receiving a first sequence of video images capturing a user seating area of the surgeon console; processing the first sequence of video images to detect a first user exiting the user seating area after detecting the first user being present at the user seating area; receiving a second sequence of video images capturing the user seating area; processing the second sequence of video images to detect a second user entering the user seating area; verifying whether the second user is the same as the first user; and determining that a user switching event has occurred at the surgeon console in response to verifying that the second user is not the same as the first user.

BRIEF DESCRIPTION OF THE DRAWINGS

The structure and operation of the present disclosure will be understood from a review of the following detailed description and the accompanying drawings in which like reference numerals refer to like parts and in which.

DETAILED DESCRIPTION

The detailed description set forth below is intended as a description of various configurations of the subject technology and is not intended to represent the only configurations in which the subject technology may be practiced. The appended drawings are incorporated herein and constitute a part of the detailed description. The detailed description includes specific details for the purpose of providing a thorough understanding of the subject technology. However, the subject technology is not limited to the specific details set forth herein and may be practiced without these specific details. In some instances, structures and components are shown in block diagram form in order to avoid obscuring the concepts of the subject technology.

Disclosed are various user-presence/absence recognition techniques based on image processing and deep learning. More specifically, various user-presence/absence recognition techniques include building/training a convolutional neural network (CNN)-based image recognition model including a user-presence/absence classifier based on training images collected from the user-seating area of a surgeon console within a robotic surgical system under various clinically-relevant conditions/cases. The trained user-presence/absence classifier can then be used during teleoperation/surgical procedures to monitor/track users in the user-seating area of the surgeon console, and continuously classify the real-time video images of the user-seating area as either a user-presence state or a user-absence state.

In some embodiments, the disclosed user-presence/absence recognition techniques can be used to detect a user-switching event at the surgeon console when a second user is detected to have entered the user-seating area after a first user is detected to have left the user-seating area. The detection of the user-switching event allows for prompting the second user in the user-seating area to identify him/herself as either the same user as the first user or a different user. If the second user is identified as a new user, the disclosed user-presence/absence recognition techniques can trigger a recalibration procedure for the new user of surgeon-console settings, including but are not limited to: user gaze-tracking settings; user UID-control settings; and user seat settings (e.g., the armrest settings).

Figure 1:
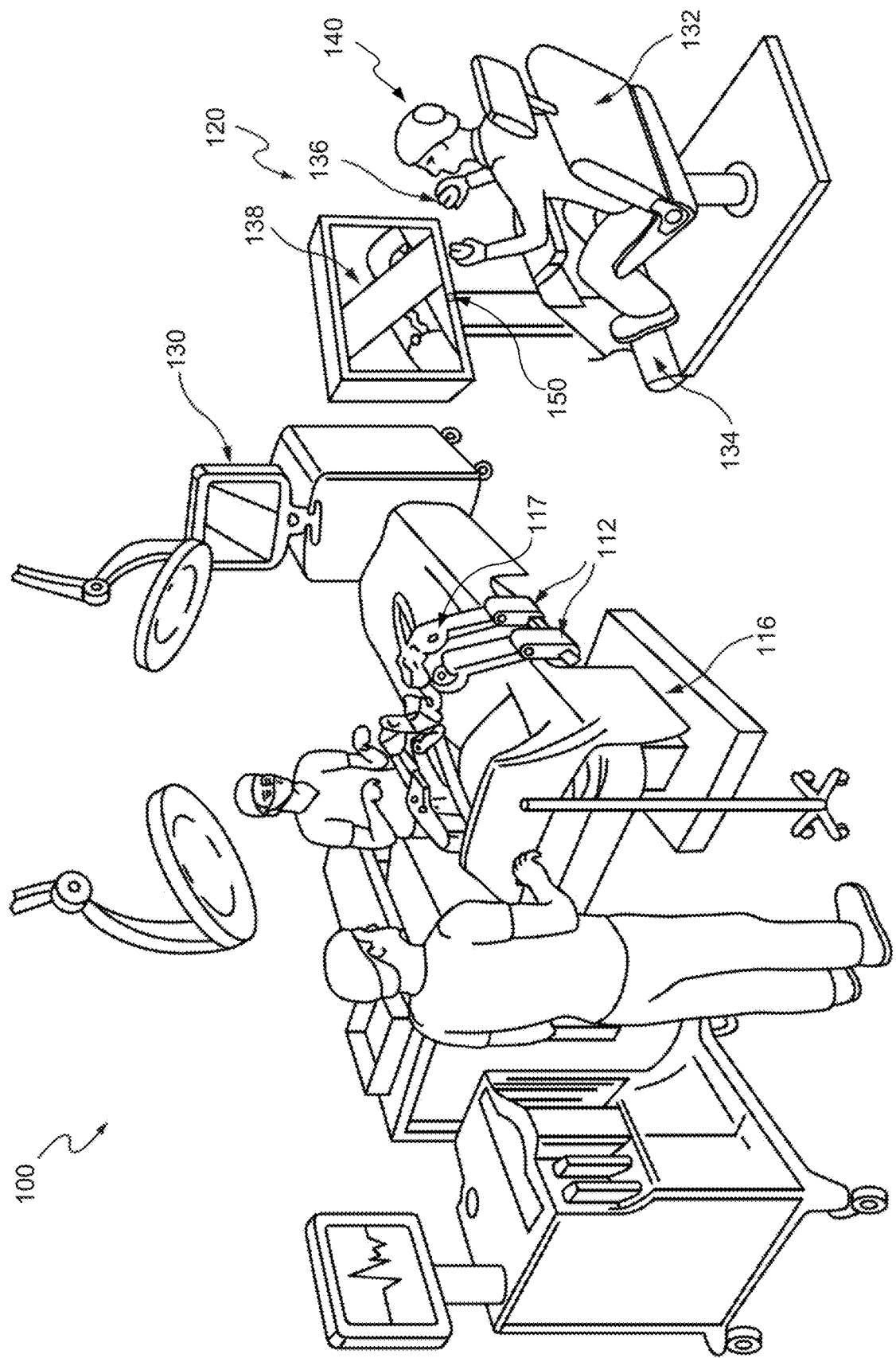
FIG. 1 shows a diagram illustrating an exemplary operating room environment with a robotic surgical system for implementing the disclosed user presence/absence recognition techniques in accordance with some embodiments described herein.

FIG. 1 shows a diagram illustrating an exemplary operating room environment with a robotic surgical system 100 for implementing the disclosed user-presence/absence recognition techniques in accordance with some embodiments described herein. As shown in FIG. 1, robotic surgical system 100 comprises a user/surgeon console 120, a control tower 130, and one or more surgical robotic arms 112 located at a robotic surgical platform 116 (e.g., a table or a bed etc.), where surgical tools with end effectors are attached to the distal ends of the robotic arms 112 for executing a surgical procedure. The robotic arms 112 are shown as a table-mounted system, but in other configurations, the robotic arms may be mounted in a cart, ceiling or sidewall, or other suitable support surface. Robotic surgical system 100 can include any currently existing or future-developed robot-assisted surgical systems for performing robot-assisted surgeries.

Generally, a user/operator 140, such as a surgeon or other operator, may use the surgeon console 120 to remotely manipulate the robotic arms 112 and/or surgical instruments (e.g., teleoperation). Surgeon console 120 may be located in the same operating room as robotic surgical system 100, as shown in FIG. 1. In other environments, surgeon console 120 may be located in an adjacent or nearby room, or teleoperated from a remote location in a different building, city, or country. Surgeon console 120 may comprise a seat 132, foot-operated controls 134, one or more handheld user interface devices (UIDs) 136, and at least one user display/monitor 138 configured to display, for example, a view of the surgical site inside a patient. As shown in the exemplary surgeon console 120, a surgeon located in the seat 132 and viewing the user display/monitor 138 may manipulate the foot-operated controls 134 and/or UIDs 136 to remotely control the robotic arms 112 and/or surgical instruments mounted to the distal ends of the arms.

In some variations, a user may also operate robotic surgical system 100 in an "over the bed" (OTB) mode, in which the user is at the patient's side and simultaneously manipulating a robotically driven tool/end effector attached thereto (e.g., with a handheld user interface device (UID) 136 held in one hand) and a manual laparoscopic tool. For example, the user's left hand may be manipulating a handheld UID 136 to control a robotic surgical component, while the user's right hand may be manipulating a manual laparoscopic tool. Thus, in these variations, the user may perform both robotic-assisted (minimally invasive surgery) MIS and manual laparoscopic surgery on a patient.

During an exemplary procedure or surgery, the patient is prepped and draped in a sterile fashion to achieve anesthesia. Initial access to the surgical site may be performed manually with robotic surgical system 100 in a stowed or withdrawn configuration to facilitate access to the surgical site. Once the access is achieved, initial positioning and/or preparation of the robotic system may be performed. During the procedure, a surgeon in the surgeon console 120 may use the foot-operated controls 134 (e.g., one or more foot pedals) and/or UIDs 136 to manipulate various surgical tools/end effectors and/or imaging systems to perform the surgery. Manual assistance may also be provided at the procedure table by sterile-gowned personnel, who may perform tasks including, but not limited to, retracting tissues or performing manual repositioning or tool exchange involving one or more robotic arms 112. Non-sterile personnel may also be present to assist the surgeon at the surgeon console 120. When the procedure or surgery is completed, robotic surgical system 100 and/or surgeon console 120 may be configured or set in a state to facilitate one or more post-operative procedures including, but not limited to, robotic surgical system 100 cleaning and/or sterilization, and/or healthcare record entry or printout, whether electronic or hard copy, such as via the surgeon console 120.

In some aspects, the communication between robotic surgical platform 116 and surgeon console 120 may be through control tower 130, which may translate user commands from the surgeon console 120 to robotic control commands and transmit them to robotic surgical platform 116. Control tower 130 may also transmit status and feedback from robotic surgical platform 116 back to surgeon console 120. The connections between robotic surgical platform 116, surgeon console 120 and control tower 130 can be via wired and/or wireless connections, and can be proprietary and/or performed using any of a variety of data communication protocols. Any wired connections may be optionally built into the floor and/or walls or ceiling of the operating room. Robotic surgical system 100 can provide video output to one or more displays, including displays within the operating room as well as remote displays accessible via the Internet or other networks. The video output or feed may also be encrypted to ensure privacy and all or portions of the video output may be saved to a server or electronic healthcare record system.

In some implementations, user/operator 140 may hold and move a UID 136 in one hand to provide input commands to move a robotic arm actuator 117 in robotic surgical system 100. This UID 136 may be communicatively coupled to the rest of the robotic surgical system 100, e.g., via a console computer system (not shown) of surgeon console 120. UID 136 may be ungrounded with respect to another component of robotic surgical system 100 while either tethered or untethered from surgeon console 120. The term "ungrounded" is intended to refer to implementations where, for example, both UIDs are neither mechanically nor kinematically constrained with respect to surgeon console 120. For example, user/operator 140 may hold a UID 136 in a hand and move freely to any possible position and orientation within space only limited by, for example, a tracking mechanism of the surgeon console. Hence, the UID 136 can generate spatial state signals corresponding to movement of the UID, e.g. position and orientation of the handheld housing of the UID, and the spatial state signals may be input signals to control a motion of robotic arm actuator 117. Robotic surgical system 100 may use control signals derived from the spatial state signals, to control proportional motion of the actuator 117. In some embodiments, the console computer system of surgeon console 120 receives the spatial state signals from the UID 136 and generates the corresponding control signals. Based on these control signals, which control how arm actuator 117 is energized to move a segment or link of a corresponding robotic arm 112, the movement of a corresponding surgical tool that is attached to the distal end of the robotic arm 112 may mimic the movement of the UID 136. Similarly, interaction between user/operator 140 and the UID 136 can generate for example, a grip control signal that causes a jaw of a grasper of the corresponding surgical tool to close and grip a tissue of a patient on top of robotic surgical platform 116.

Robotic surgical system 100 may include multiple UIDs 136, where respective control signals are generated for each UID 136 that control the actuators and the surgical tool (end effector) attached to a respective arm 112. For example, user/operator 140 may move a first UID 136 (e.g., the left UID) in one hand (e.g., the left hand) to control the motion of an arm actuator 117 that is in a left robotic arm 112, where the actuator responds by moving linkages, gears, etc., in the left robotic arm 112. Similarly, user/operator 140 may move a second UID 136 (e.g., the right UID) in the other hand (e.g., the right hand) to control the motion of another arm actuator 117 that is in a right robotic arm 112, which in turn moves other linkages, gears, etc., in the right robotic arm 112. Motions of a respective actuator 117 in a respective robotic arm 112 can be controlled by the spatial state signals generated from a respective UID 136. When user/operator 140 has finished manipulating the surgical tools with the UIDs 136, the user/operator may dock (i.e., store/rest) the UIDs 136 at designated docking areas/docking stations located at console 120. For example, surgeon console 120 may include docking stations located at each of the left and right armrests (not shown) of seat 132. To dock the left and right UIDs 136, the user may move the left UID 136 to the left docking station and the right UID 136 to the right docking station, and place each of the UIDs in their respective docking station holder.

To detect user presence at or user absence from surgeon console 120 (or "console 120" hereinafter), video images of a user-seating area of console 120 can be captured and analyzed. In the scope of console 120, the user-seating area in this patent disclosure generally refers to surgeon seat 132, which can be with or without user/operator 140. In some embodiments, images of the user-seating area can be captured by a camera installed on or integrated with user display/monitor 138 (also referred to as "monitor 138" or "the monitor" hereinafter) and aimed at/pointed to the user-seating area and seat 132. For example, a camera 150 may be located in the middle of the bottom bezel portion of monitor 138. A person of ordinary skill in the art will appreciate that images taken of the user-seating area by camera 150 can be classified into two types: the first type of images mostly comprise mostly seat 132 and a background behind seat 132, but without any user/operator seating in seat 132. We classify the first type of images as a "user-absence state," or "user-absence classification." Alternatively, the second type of images taken of the user-seating area by camera 150 will comprise mostly a user/operator 140 seating in seat 132 (wherein the seat itself is often blocked), and a background behind seat 132. We classify the second type of images as a "user-presence state" or "user-presence classification." As will be discussed in more detail below, the disclosed user-presence/absence classifier is configured to recognize/distinguish the two types of seating area images and classify any given user-seating area image into either the user-absence classification or the user-presence classification.

Figure 2:
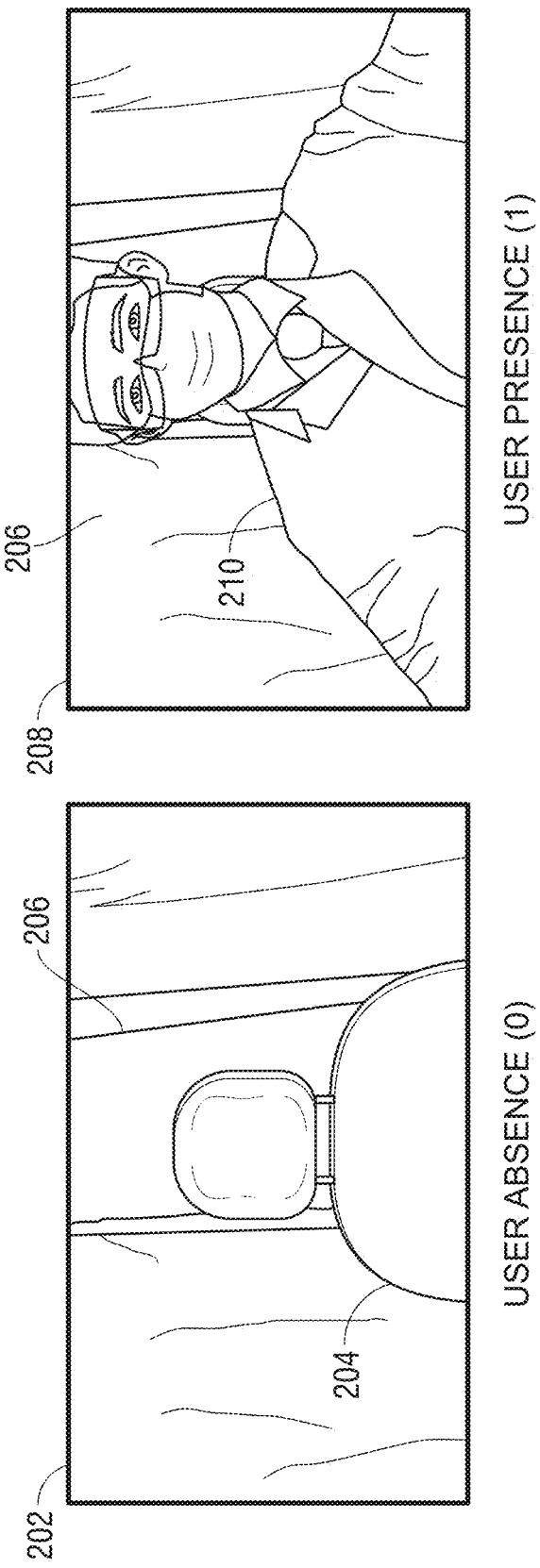
FIG. 2 presents two exemplary video images of a user-seating area illustrating a user-absence state and a user-presence state of the user-seating area during a surgical procedure in accordance with some embodiments described herein.

FIG. 2 presents two exemplary video images of a user-seating area 200 illustrating a user-absence state and a user-presence state of the user-seating area during a surgical procedure in accordance with some embodiments described herein. For example, the left image 202 in FIG. 2 is a user-seating area image associated with the user-absence state because there is no user or any person in image 202. More specifically, left image 202 shows a console seat 204 including a seat back (the upper portion of the seat) and a headrest/head-holder in front of a background 206. Note that for training purposes, image 202 will be labeled with the user-absence classification, e.g., using a label "A" or a binary number "0." For user recognition purposes, the disclosed user-presence/absence classifier is configured to automatically classify image 202 with the user-absence classification. In contrast, the right image 208 in FIG. 2 is a user-seating area image associated with the user-presence state. More specifically, right image 208 shows a user 210 seating in console seat 204 in front of background 206, whereas console seat 204 in image 208 is mostly blocked by user 210. Note that for training purposes, image 208 will be labeled with a user-presence classification, e.g., using a label "P" or a binary number "1." For user recognition purposes, the disclosed user-presence/absence classifier is configured to automatically classify image 208 with the user-presence classification.

Note that video image 202 is just one example out of many possible variations for the user-absence state and video image 208 is just one example out of many possible variations for the user-presence state. As will be discussed in more detail below, there are also some less obvious, in-between situations compared to video images 202 and 208, e.g., during the time periods when a user is leaving/exiting or returning/entering the user-seating area. The disclosed user-presence/absence recognition techniques are also configured to detect such cases and provide proper classifications for these cases.

The disclosed user-presence/absence recognition techniques include both a user-presence/absence recognition model building system for constructing a CNN-based user-presence/absence classifier based on training images collected from a user-seating area of a surgeon console under various clinically-relevant conditions/cases. The disclosed user-presence/absence recognition techniques also include a user-presence/absence tracking procedure based on the trained user-presence/absence classifier to automatically recognize video images of the user-seating area as either the user-presence state or the user-absence state during a surgical procedure and trigger proper interactions with a current user if a transitional event from the user-absence state to the user-presence state (i.e., a potential user switching event) is detected.

Figure 3:
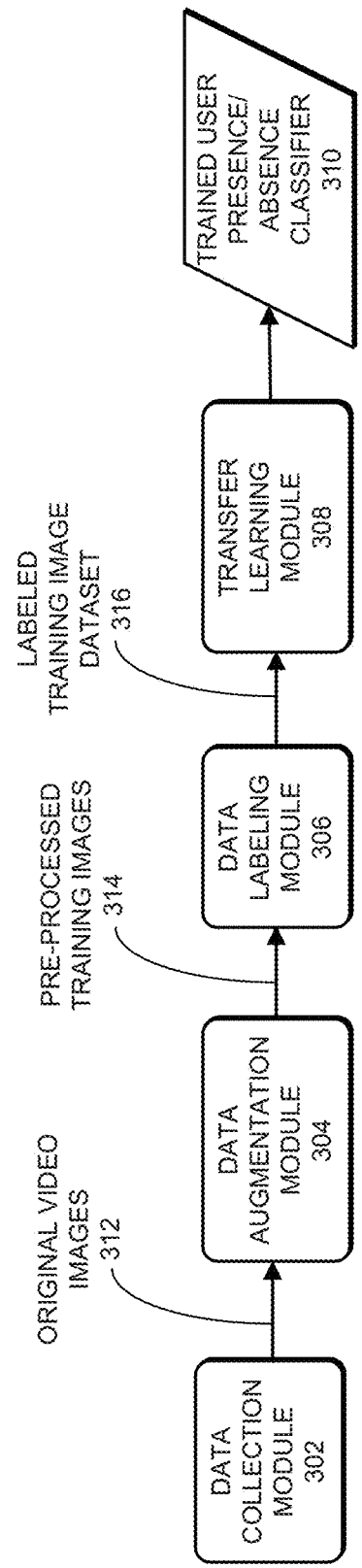
FIG. 3 illustrates a block diagram of the disclosed user-presence/absence recognition model building system for building a CNN-based user-presence/absence classifier based on video images of the user-seating area in accordance with some embodiments described herein.

FIG. 3 illustrates a block diagram of a user-presence/absence recognition model building system 300 for building a CNN-based user-presence/absence classifier based on video images of the user-seating area in accordance with some embodiments described herein. As shown in FIG. 3, user-presence/absence recognition model building system 300 (also referred to as "model building system 300" hereinafter) can include a data collection module 302, a data augmentation module 304, a data labeling module 306, a transfer learning module 308, which are coupled in the manner shown. Note that model building system 300 generates a trained user-presence/absence classifier 310 as its output.

In some embodiments, data collection module 302 in model building system 300 obtains a diverse set of raw/original video images 312 of a user-seating area of a surgeon console under various clinically-relevant conditions/cases. These various clinically-relevant cases can include various backgrounds of the user-seating area, for example: different background colors (e.g., white, light blue, etc.) and backgrounds with/without people. The various clinically-relevant cases can also include different lighting conditions of the user-seating area. The various clinically-relevant cases can further include various screen angles of monitor 138, including but are not limited to a straight-on angle and various tilted angels. The various clinically-relevant cases of the user-seating area can also include various heights of monitor 138.

The various clinically-relevant cases of the user-seating area can further include different distances between user 140 and monitor 138, e.g., a number of distances within a range from 20-cm to 100-cm. The various clinically-relevant cases of the user-seating area can also include status of UIDs 136, wherein the status can include stationary UIDs 136 (i.e., when UIDs 136 are docked/laid down) and moving UIDs 136 (i.e., when UIDs 136 are in teleoperation use in the user's hands). The various clinically-relevant cases of the user-seating area can further include user swap events (i.e., events wherein a first user exits the user-seating area followed by a second user enters the user-seating area). The various clinically-relevant cases of the user-seating area can also include various durations of captured video clips of the user-seating area for acquiring training images 312, e.g., between 30-60 seconds.

The various clinically-relevant cases of the user-seating area can include different scenarios related to whether user 140 wears or does not wear one or more of the following items on her/his head: QR tags, a face mask, and a three-dimensional (3D) headset. The various clinically-relevant cases of the user-seating area can also include different scenarios related to whether user 140 wears or does not wear a scrub. The various clinically-relevant cases of the user-seating area can also include different scrub color user 140 is wearing, e.g., a white color or a light blue. The various clinically-relevant cases of the user-seating area can further include various headrest angles of seat 132. The various clinically-relevant cases of the user-seating area can also include various types of head movements of user 140, e.g., moving to the left, to the right, as well as up and down movements. The various clinically-relevant cases of the user-seating area can also include multiple different types of surgeon console seats. Last but not least, the various clinically-relevant cases of the user-seating area can include collecting user-seating area images from different surgeon consoles of different robotic surgical systems. Note that data collection module 302 can collect video images 312 of the user-seating area including some or all of the above-described types of clinically-relevant scenarios/cases, as well as other types of clinically-relevant scenarios/cases not listed above. Moreover, because all captured images of the user-seating area are to be classified as either the user-presence state or the user-absence state, original video images 312 generated by data collection module 302 should include sufficient number of training images of each of the two image classifications.

Figure 4:
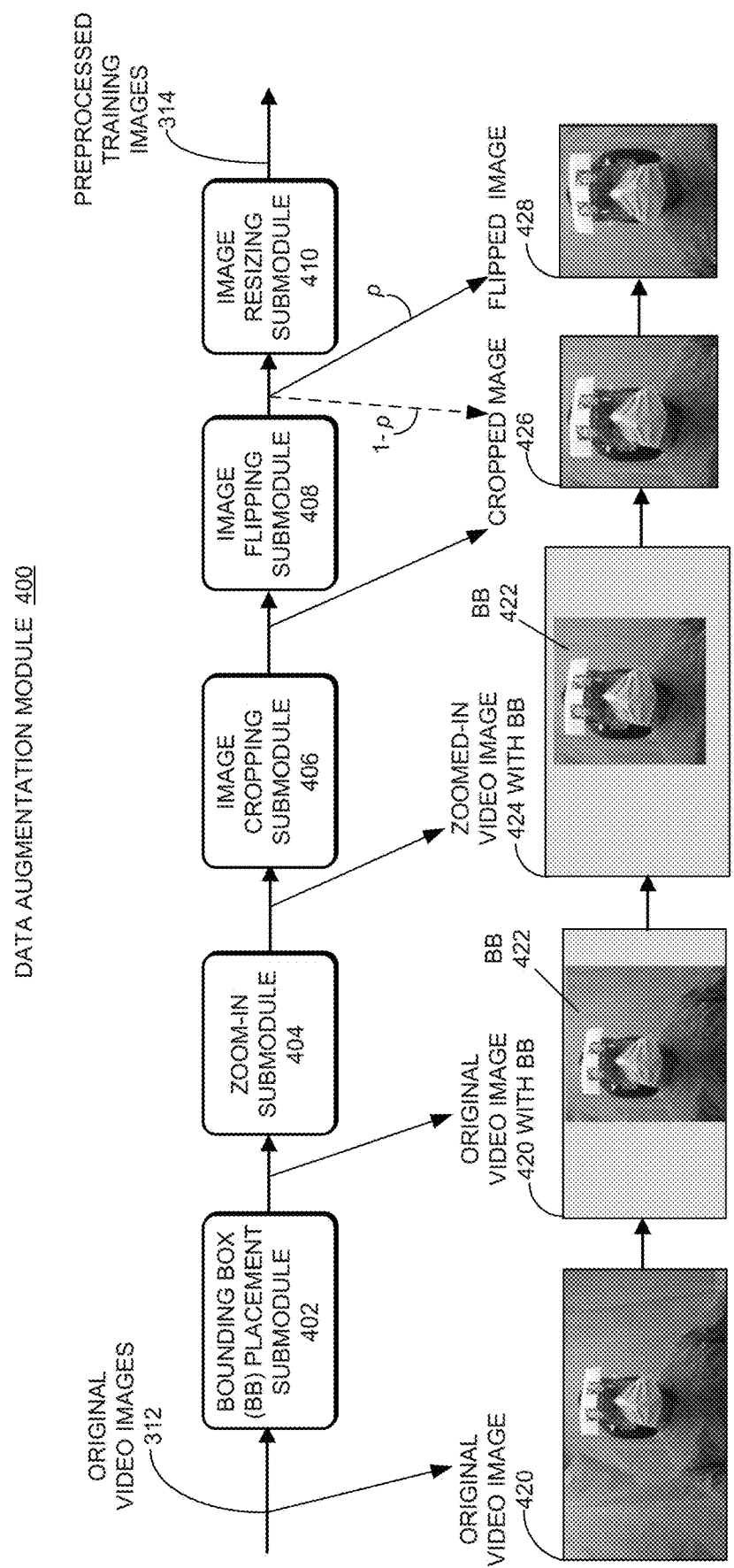
FIG. 4 illustrates a block diagram of an exemplary implementation of the disclosed data augmentation module in the disclosed user-presence/absence recognition model building system in accordance with some embodiments described herein.

In some embodiments, data augmentation module 304 in model building system 300 is configured to receive original video images 312 (also referred to as the "raw images 312" hereinafter), preprocess the received raw images and generate preprocessed training images 314. FIG. 4 illustrates a block diagram of an exemplary implementation 400 of data augmentation module 304 in accordance with some embodiments described herein. As can be seen in FIG. 4, the input to data augmentation module 400 is an original video image 312 captured by camera 150 of the user-seating area. FIG. 4 shows an exemplary original video image 420 of a user-seating area as an example of original video image 312, wherein video image 420 captures a user seating in front of a background. In this particular example, video image 420 is a high definition image with a 16:9 aspect ratio. However, other examples of original video image 312 can have other image format different from the example image 420.

In FIG. 4, an original video image 312 is received by a bounding box placement submodule 402, which is configured to randomly place a bounding box of predetermined dimensions within the frame of original video image 312. In some embodiments, the predetermined dimensions of the bounding box used by submodule 402 are determined based on the largest bounding box that can fit inside original video image 312. Because many CNN image recognition models require square input images, preparing CNN input images for either model training or image detection/recognition requires cropping out square images from the original non-square video images. Hence, in some embodiments, the largest bounding box that can fit inside a non-square original video image 312 is also a square image which has both the vertical dimension and the horizontal dimension equal to the smaller dimension (of the two dimensions) of original video image 312. For example, FIG. 4 also shows randomly placing a largest square bounding box 422 inside the exemplary video image 420. In this example, because bounding box 422 already fills the full vertical extent of video image 420, bounding box placement submodule 402 implements the degree of randomness of placing the bounding box 422 only in the horizontal direction, which is shown to be off-centered toward the right border of video image 420. However, the proposed randomness in placing bounding box 422 means that bounding box 422 can be located inside video image 420 anywhere between the left border and the right border of video image 420.

Bounding box placement submodule 402 in data augmentation module 400 is followed by a zoom-in submodule 404 which is configured to randomly zoom in on original video image 312 by a random factor. For example, FIG. 4 also illustrates the effect of zooming in on original video image 420 by a random factor on both video image 420 and bounding box 422. As can be seen in FIG. 4, the zoom-in operation increases the size of original video image 420 by the random factor to create a larger zoomed-in video image 424, whereas the size of bounding box 422 within zoomed-in video image 424 remains unchanged. However, as can be clearly observed from zoomed-in video image 424, the portion of the image inside bounding box 422 now corresponds to a smaller portion of original video image 420 than the portion of image inside the same bounding box 422 placed inside original video image 312 prior to applying the zoom-in effect by zoom-in submodule 404.

Zoom-in submodule 404 in data augmentation module 400 is further followed by an image cropping submodule 406, which is configured to crop out the portion of the zoomed-in video image outputted by zoom-in submodule 404 inside the placed bounding box, and as a result to generate a cropped image. For example, FIG. 4 illustrates the effect of image cropping submodule 406, which includes cropping out the portion of zoomed-in video image 424 inside bounding box 422 to obtain a cropped image 426. Image cropping submodule 406 in data augmentation module 400 is further followed by an image flipping submodule 408 which is configured to flip the cropped image from the previous stage horizontally with a predetermined probability p (e.g., p=50%) to generate either a flipped version of the cropped image or the original cropped image. For example, FIG. 4 shows the effect of flipping cropped image 426 horizontally to generate a flipped image 428. Note that because image flipping submodule 408 only performs the image clipping operation based on the predetermined probability p (p∈(0, 1)), the output of image flipping submodule 408 does not have to include the flipping effect, i.e., it can also output cropped image 426 instead of flipped image 428.

Finally in data augmentation module 400, image flipping submodule 408 is followed by image resizing submodule 410 configured to resize the output image of image flipping submodule 408 to the predetermined dimensions of a downstream CNN image recognition model. For example, the predetermined dimensions in image resizing submodule 410 can be 299×299 if the downstream CNN model is an Inception-v3 model. Eventually, data augmentation module 400 outputs a preprocessed training image 314 for the original input video image 312 with the predetermined dimensions, such as 299×299.

As described above, each of bounding box placement submodule 402 and zoom-in submodule 404 within the disclosed data augmentation module 400 can be configured with a degree of randomness. Moreover, image flipping submodule 408 operates based on the predetermined probability p and therefore can have two different outcomes. Consequently, the combined randomness and probability of data augmentation module 400 ensures that each time the same input video image 312 is passed through data augmentation module 400, data augmentation module 400 will almost always generate a different preprocessed training image 314. In some embodiments, for each original video image 312 in the set of original video images 312 generated by data collection module 302, image 312 is passed through data augmentation module 400 multiple times to generate multiple preprocessed training images 314 based on the same original image 312. As such, a single original image 312 can be used to generate a diverse set of augmented training images 314. Note that because the amount of original/raw training images 312 collected by data collection module 302 are often limited due to time and resource constraints, the disclosed data augmentation module 400 allows for generating a sufficiently large and diverse training dataset based on a smaller set of original video images 312, thereby saving both time and resources required to collect raw training images 312.

Referring back to FIG. 3, note that data augmentation module 304 in model building system 300 is coupled to data labeling module 306, which is configured to receive preprocessed training images 314 and subsequently label each training image in preprocessed training images 314 with either the user-absence classification, e.g., using a label "A" or a binary number "0," or the user-presence classification, e.g., using a label "P" or a binary number "1." Note that data labeling module 306 generates a labeled training image dataset 316 as output.

Referring back to FIG. 2, note that while exemplary video images 202 and 208 represent more common and obvious cases of the user-absence state images and the user-presence state images, respectively, there are many different scenarios/variations of the user-presence state which are not as obvious as image 208 for receiving a user-presence classification. For example, a user in a given image may be off-centered and/or only partially visible. Similarly, there are also many different scenarios/variations of the user-absence state which are not as obvious as image 202 for receiving a user-absence classification. For example, a part of a user's body may be visible in a given image but the user is clearly not in the seat shown within the image. In some embodiments, data labeling module 306 in FIG. 3 is configured to label each preprocessed training image 314 based on the following rules: an image showing a fully-visible seat (i.e., no part of the seat is blocked by a portion of a user's body) is labeled with a user-absence classification; whereas an image showing a partially-visible or non-visible seat (i.e., any part of the seat is blocked by a user's body) is labeled with a user-presence classification.

Figure 5:
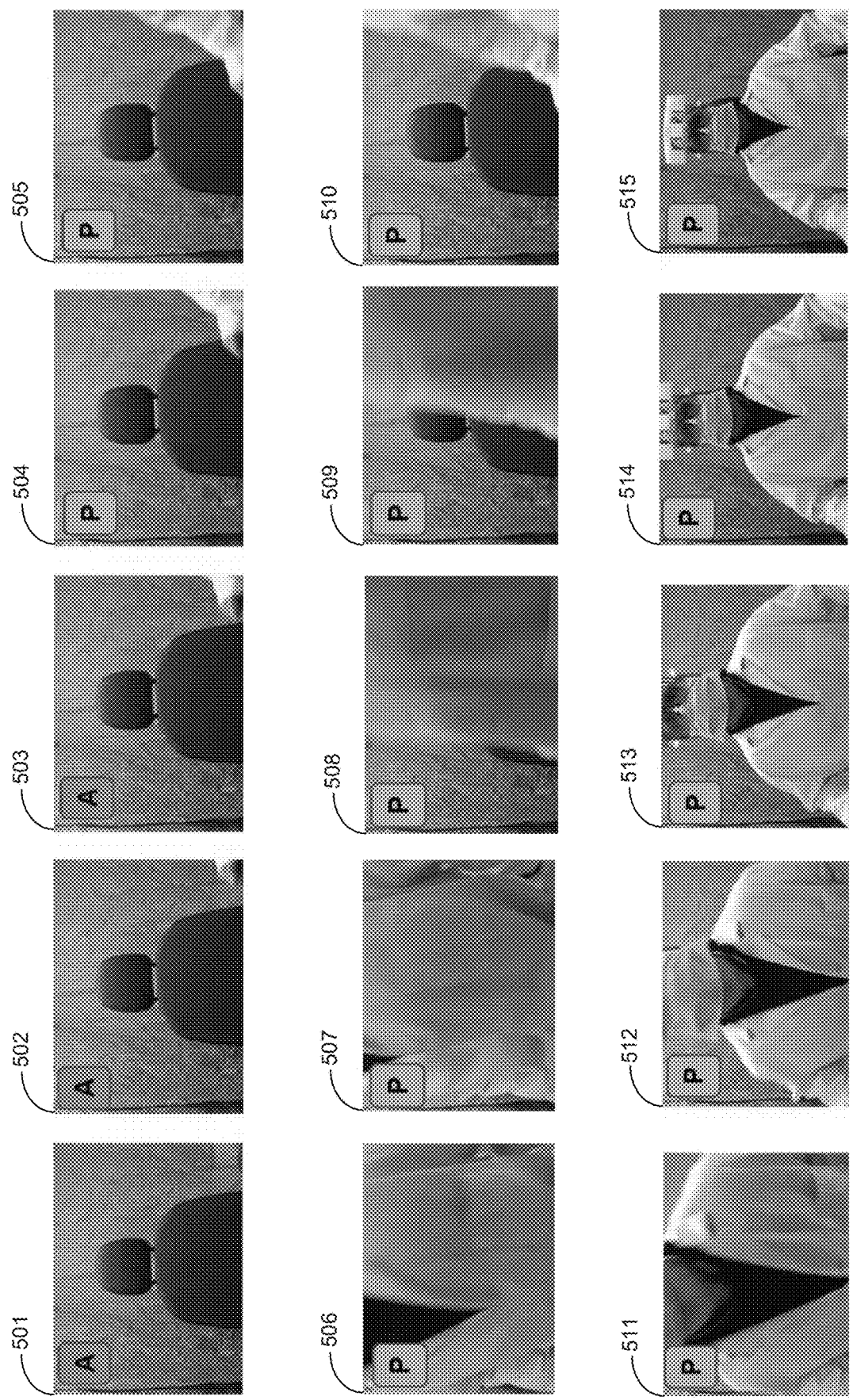
FIG. 5 illustrates an exemplary process of labeling a time-sequence of video images as either the user-presence classification or the user-absence classification in accordance with some embodiments described herein.

FIG. 5 illustrates an exemplary process of labeling a time-sequence of video images as either the user-presence classification or the user-absence classification in accordance with some embodiments described herein. As can be seen in FIG. 5, a sequence of 15 video images 501-515 represents 15 consecutive video frames of a video clip illustrating an event where a user entering a user seating area and taking a seat. Note that video images 501-503 have been labeled with "A," i.e., the user-absence classification. This is because these three video images showed a fully-visible seat, even if a part of the user's body is visible in some of the above images. Also note that images 504-515 have been labeled with "P," i.e., the user-presence classification. This is because these twelve video images showed either a partially-visible/partially-blocked seat or non-visible fully-blocked seat.

In some embodiments, the above-described labeling process can be fully automatic by constructing a machine-learning-based object recognition model trained to detect and recognize a fully-visible/unblocked seat in the user-seating area. For example, this proposed object recognition model can be separately trained on training images of various configurations of fully-visible/unblocked seats under various user-seating area conditions (e.g., under different backgrounds, lighting conditions, and possible seat angles relative to the monitor/camera). When implementing this object recognition model into data labeling module 306 in model building system 300, data labeling module 306 can then apply the trained object recognition model to each preprocessed training image 314 and automatically generate a binary decision and a corresponding label/classification for the training image 314, i.e.: (1) fully-visible-seat is-recognized decision and the corresponding user-absence label/classification; or (2) fully-visible-seat not-recognized decision and the corresponding user-presence label/classification.

Referring back to FIG. 3, note that data labeling module 306 in model building system 300 is coupled to transfer learning module 308, which is configured to receive the labeled training image dataset 316, train a CNN-based user-presence/absence classifier within transfer learning module 308 based on the labeled training image dataset 316, and subsequently generate trained user-presence/absence classifier 310 as output. In some embodiments, transfer learning module 308 employs a trained CNN-based image-recognition model to perform transfer learning for user-presence/absence recognition purposes. More specifically, transfer learning module 308 can be configured to "freeze" all layers in the trained CNN-based image-recognition model except for the last few layers. Note that the trained CNN-based image-recognition model can be a well-known or otherwise previously-established image recognition model for other objection recognition applications, such as for face recognition. In some embodiments, the phrase "freezing all layers in the trained model except for the last few layers" means freezing all layers from the very first layer of the trained CNN-based model up to the bottleneck layer of the trained CNN-based model, except for the final two layers: i.e., a fully-connected layer and a Softmax layer after the bottleneck layer. Note that the term "freezing a given layer" in the trained CNN-based image-recognition model herein means fixing the previously-established parameters in the given layer, including the weights and biases of the given layer in the disclosed transfer learning module 308. In the above example, performing transfer learning using the trained CNN-based image-recognition model within transfer learning module 308 means fixing the previously-established weights and biases of all network layers of the trained CNN-based model up to and including the bottleneck layer, but without fixing the trainable parameters in the final fully-connected layer and Softmax layer of the trained CNN-based model.

Figure 6:
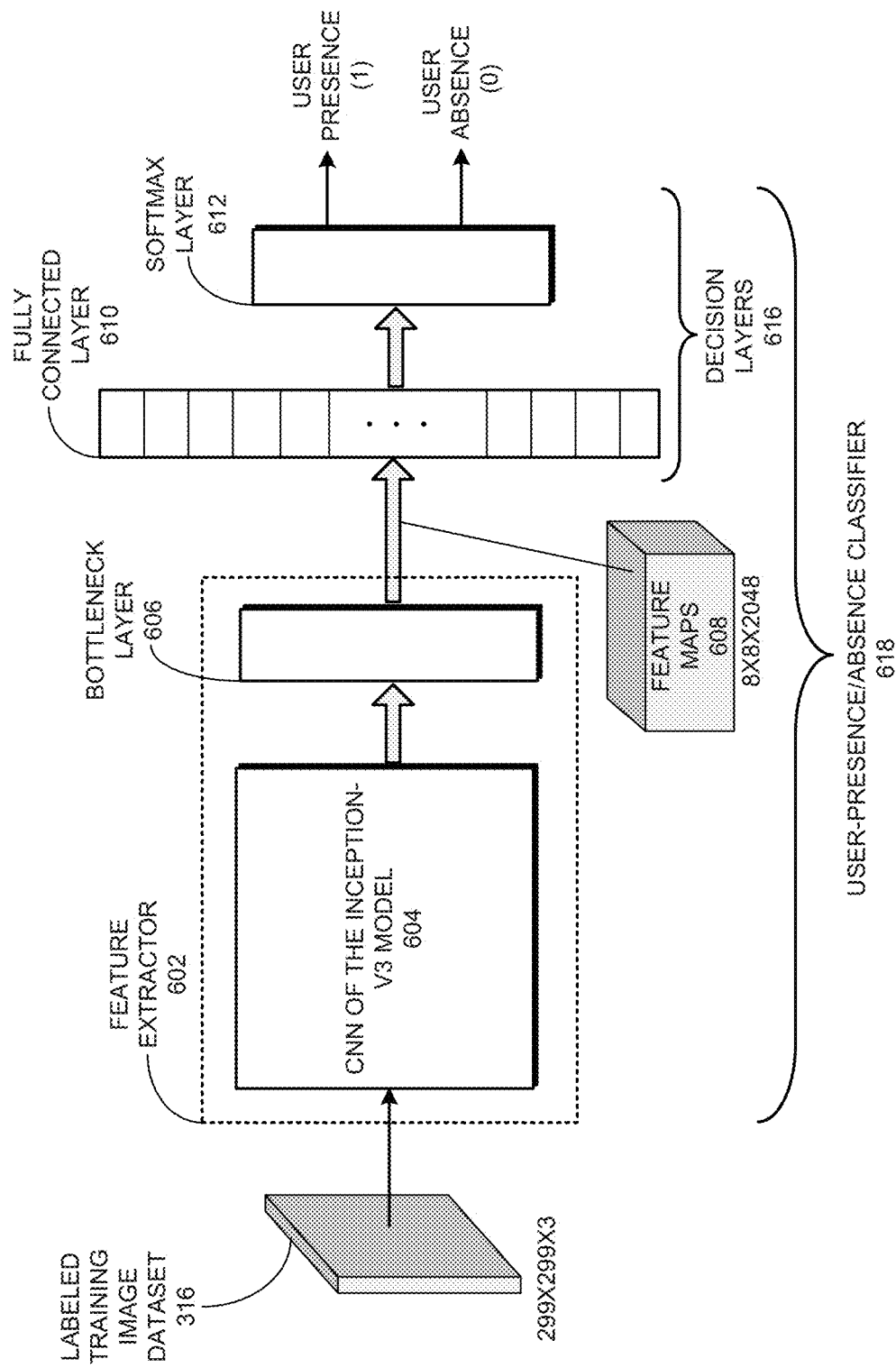
FIG. 6 illustrates an exemplary implementation of the disclosed transfer learning module based on using the Inception-v3 image-recognition model in accordance with some embodiments described herein.

FIG. 6 illustrates an exemplary implementation 600 of transfer learning module 308 based on using the Inception-v3 image-recognition model in accordance with some embodiments described herein. As can be seen in FIG. 6, transfer learning module 600 includes a feature extractor 602 which is composed of the entire Inception-v3 image-recognition model (or "Inception-v3 model" hereinafter) except the final fully-connected (FC) layer and Softmax layer of the original Inception-v3 model. More specifically, feature extractor 602 includes CNN 604 of the Inception-v3 model that includes all layers of the Inception-v3 model up to and before the bottleneck layer. Note that CNN 604 is composed of a stack of feature-extraction layers including a sequence of convolutional layers interleaved with a sequence of pooling layers. For transfer learning purposes in transfer learning module 600, parameters such as weights and biases in all layers within CNN 604 are fixed to the trained values of the Inception-v3 model. In feature extractor 602, CNN 604 of feature extractor 602 is followed by the bottleneck layer 606 of the original Inception-v3 model. For performing transfer learning in transfer learning module 600, parameters such as weights and biases in bottleneck layer 606 are also fixed to the trained values of the Inception-v3 model.

Feature extractor 602 of transfer learning module 600 receives the labeled training image dataset 316 (in reference to the same items in FIG. 3) as inputs, wherein each input image in the labeled training image dataset 316 has been resized to 299×299×3 (3 channels) based on the input-size requirements of the Inception-v3 model. Using feature extractor 602 with fixed parameters, transfer learning module 600 extracts a set of feature maps 608 as the outputs of bottleneck layer 606 for each input training image 316. In some embodiments, feature maps 608 for each input training image 316 has a dimension of 8×8×2048.

Note that because the parameters in feature extractor 602 are fixed, feature extractor 602 will always generate the same set of feature maps 608 for the same input training image 316. In some embodiments, transfer learning module 600 can use the same labeled training image dataset 316 multiple times, referred to as multiple "epochs of trainings," and in each epoch of training, the same labeled training image dataset 316 is used to train the user presence/absence classifier. Because the outputted sets of feature maps 608 do not change in different epochs of trainings based on the same training image dataset 316, the sets of feature maps 608 of the labeled training image dataset 316 can be stored as two-dimensional (2D) images in a memory or a hard disk after the first epoch of training. As a result, during the second and subsequent epochs of trainings, the sets of feature maps 608 can be simply retrieved from the memory or the disk instead of having to be recalculated by passing the same training image dataset 316 through feature extractor 602, thereby saving both training time and computational resources during the transfer learning.

Note that transfer leaning module 600 does not include the original final FC layer and Softmax layer of the original Inception-v3 model. Instead, transfer leaning module 600 uses a customized FC layer 610 with a set of variables and a customized Softmax layer 612 as the decision layers 616 of the disclosed user-presence/absence classifier 618. As shown in FIG. 6, user-presence/absence classifier 618 includes both feature extractor 602 and decision layers 616.

As can be seen in FIG. 6, customized FC layer 610 receives the sets of feature maps 608 of the processed training image dataset 316 as inputs, which are used to train the set of variables within the customized FC layer 610. In some embodiments, customized FC layer 610 can include 512 nodes, and each of the 512 nodes is associated with a weight variable and a bias variable. As mentioned above, training the customized FC layer 610 can include performing multiple epochs of trainings (e.g., epoch=20) using the same sets of feature maps 608 extracted from the same training image dataset 316. After performing the multiple epochs of trainings, the customized FC layer 610 will include a set of trained parameters. For the above example of 512 nodes in the FC layer 610, the set of trained parameters would include 512 trained weight values and 512 trained bias values.

Finally in transfer leaning module 600, the outputs from customized FC layer 610 are coupled to Softmax layer 612 which includes a binary Softmax function configured to generate user-presence (e.g., with binary value 1) or user-absence (e.g., with binary value 0) classifications/decisions for each input training image 316. Note that after the customized FC layer 610 has been sufficiently trained, e.g., through multiple epochs of trainings based on the training image dataset 316, the trained variables within the customized FC layer 610 can be fixed and the trained user-presence/absence classifier 618 becomes the trained user presence/absence classifier 310 which is the output of user-presence/absence recognition model building system 300.

Note that although transfer learning module 308/600 has been described based on using the Inception-v3 model as the trained feature extractor, the disclosed transfer learning module within the disclosed user-presence/absence recognition model building system 300 is not meant to be limited to using a particular trained deep-learning framework. Generally speaking, the trained feature extractor within the disclosed transfer learning module 308/600 can be implemented with other known image-recognition models including, but are not limited to GGNet, ResNet, DenseNet, AlexNet, Dual Pathway Network, MobileNet, and Inception v1-v2.

Figure 7:
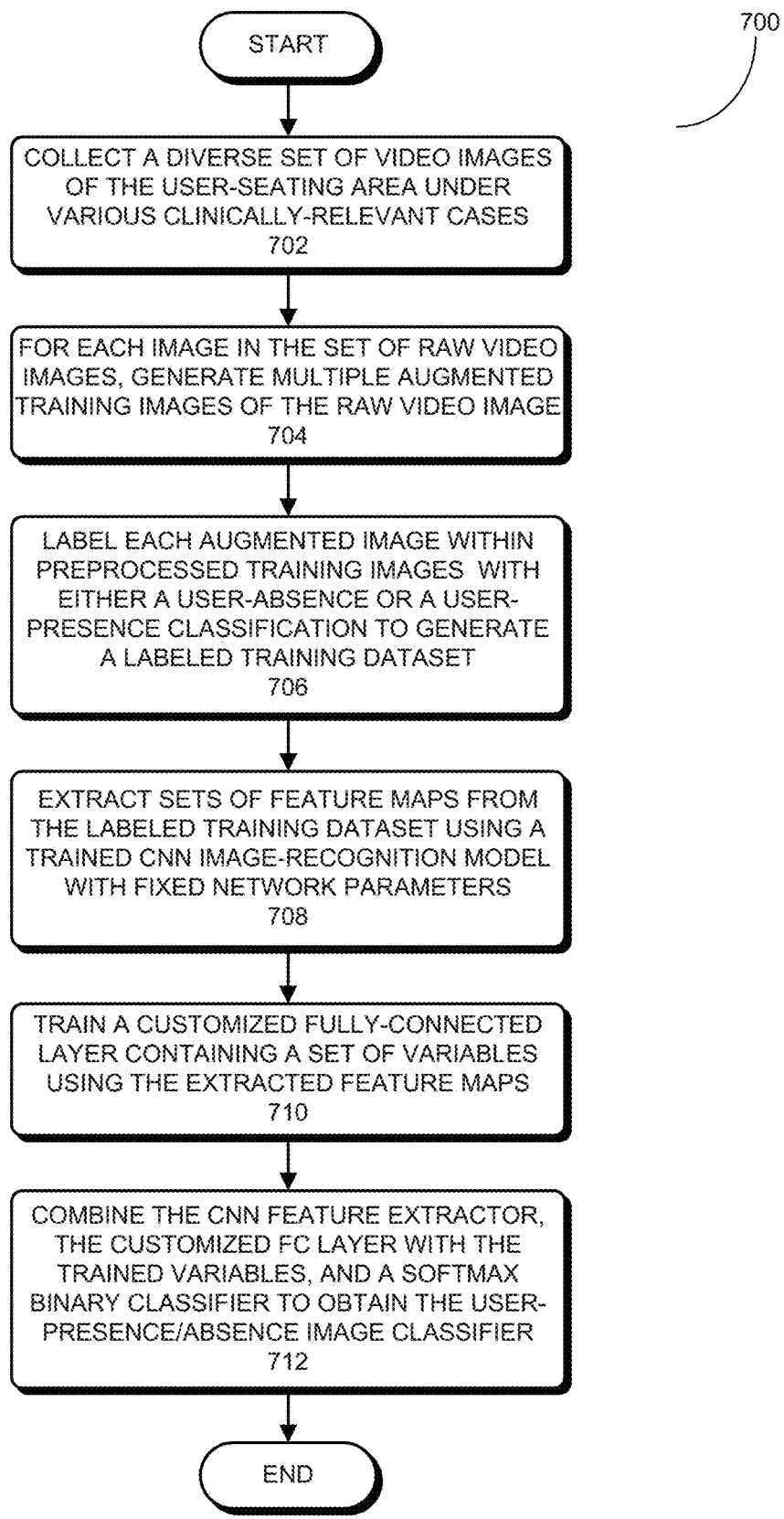
FIG. 7 presents a flowchart illustrating an exemplary process for building a CNN-based user-presence/absence classifier based on captured video images of the user-seating area in accordance with some embodiments described herein.

FIG. 7 presents a flowchart illustrating an exemplary process 700 for building a CNN-based user-presence/absence classifier based on captured video images of the user-seating area in accordance with some embodiments described herein. In one or more embodiments, one or more of the steps in FIG. 7 may be omitted, repeated, and/or performed in a different order. Accordingly, the specific arrangement of steps shown in FIG. 7 should not be construed as limiting the scope of the technique.

Process 700 may begin by collecting a diverse set of raw video images of the user-seating area under various clinically-relevant cases (step 702). For example, these various clinically-relevant cases can include various backgrounds of the user-seating area; different lighting conditions of the user-seating area; various screen angles and height of the monitor, different distances between the user and the monitor; status of the UIDs; whether the user wears or does not wear one or more of the following items: QR tags, a face mask, a 3D headset, and a scrub; different scrub colors; various headrest angles of the seat; various types of head movements of the user, among others.

Next, for each raw video image in the diverse set of raw video images of the user-seating area, process 700 generates a diverse set of augmented/preprocessed training images of the raw video image (step 704). For example, the diverse set of augmented/preprocessed training images of the raw video image can include one or multiple of the following augmented images: (1) one or more cropped images obtained from the raw video image by first randomly placing the largest square bounding box inside the raw image and then cropping the raw image using the bounding box; (2) one or more cropped and zoomed-in images obtained from the raw video image by first randomly placing the largest square bounding box inside the raw image; then randomly zooming in the raw image by a random factor; and finally cropping the zoomed-in image using the bounding box; and (3) one or more cropped, zoomed-in, and possibly flipped images obtained from the raw video image by first randomly placing the largest square bounding box inside the raw video image; then randomly zooming in the raw image by a random factor; next cropping the zoomed-in image using the bounding box, and finally flipping the cropped-out image horizontally with a predetermined probability. In some embodiments, each of the diverse set of augmented/preprocessed training images of a given raw video image is resized to the predetermined dimensions required by the input-size constraints of a downstream CNN classifier to be trained.

Next, for the diverse sets of augmented/preprocessed training images generated from the set of raw video images, process 700 labels each preprocessed training image with either the user-absence classification or the user-presence classification (step 706). In some embodiments, process 700 labels a preprocessed training image with the user-absence classification if the preprocessed image shows a fully-visible seat; or with the user-presence classification if the preprocessed image shows a partially-visible or non-visible seat. After labeling the set of preprocessed training images, process 700 generates a labeled training image dataset for the downstream user-presence/absence classifier.

Subsequently, process 700 trains a CNN-based user-presence/absence classifier with the labeled training image dataset through transfer learning. Specifically, process 700 first extracts sets of feature maps from the labeled training image dataset using a trained CNN image-recognition model with fixed network parameters (also referred to as the "feature extractor") (step 708). In some embodiments, the trained CNN image-recognition model is the Inception-v3 image-recognition model up to the bottleneck layer and without the original final FC layer and Softmax layer of the Inception-v3 model. Next, process 700 trains a customized FC layer containing a set of variables using the extracted sets of feature maps (step 710). In some embodiments, process 700 trains the customized FC layer by performing multiple epochs of trainings with the same extracted sets of feature maps of the same labeled training image dataset. Finally, process 700 combines the fixed-parameter CNN feature extractor, the customized FC layer with the set of trained variables, and a Softmax binary classifier to obtain a disclosed user-presence/absence image classifier (step 712).

Figure 8:
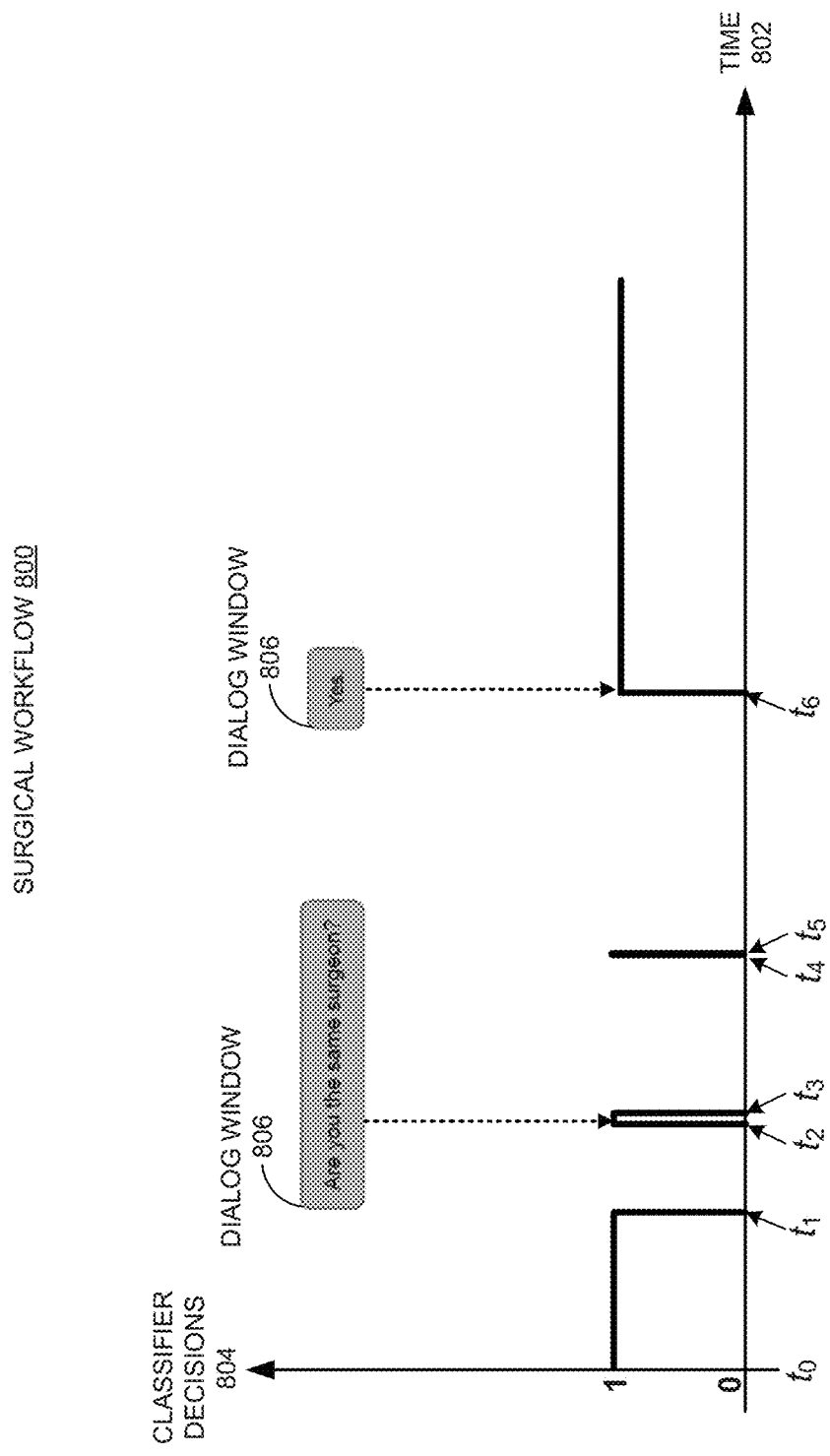
FIG. 8 illustrates an exemplary surgical workflow which tracks users at a surgeon console during a surgical session using the trained user-presence/absence image classifier in accordance with some embodiments described herein.

FIG. 8 illustrates an exemplary surgical workflow 800 which tracks users at a surgeon console during a surgical session using the disclosed (trained) user-presence/absence classifier in accordance with some embodiments described herein. As can be seen in FIG. 8, surgical workflow 800 is represented by a time plot with time 802 in the horizontal axis and classifier decisions 804 of the trained user-presence/absence classifier (hereinafter "user-presence/absence classifier") in the vertical axis. More specifically, the user-presence/absence classifier, such as trained user-presence/absence classifier 310 generated by user-presence/absence recognition model building system 300 is used to receive and process real-time video images of the user seating area of the surgeon console. For each frame of the real-time video images, user-presence/absence classifier generates a binary decision 804 of either a user-presence decision (i.e., value 1 in the vertical axis) or a user absence decision (i.e., value 0 in the vertical axis).

Note that surgical workflow 800 is integrated with a user-switching detection mechanism designed to detect the event when a new user enters the user seating area after a previous user has left the user seating area. As will be discussed below in more detail, the disclosed user-switching detection mechanism can further interact with the user just entering the user seating area to determine whether this user is the same user as the previous user. If the user confirms that he/she is not the same user as the previous user, the disclosed user-switching detection mechanism can trigger recalibration or reconfiguration of surgeon console settings, such as user gaze-tracking settings, user UID-control settings, and user seat settings (e.g., the armrest settings) for the new user.

We now begin describing surgical workflow 800 in more detail in conjunction with the user-switching detection mechanism.

Note that surgical workflow 800 begins with a first time period from to to during which time user-presence/absence classifier outputs user-presence decisions (1), indicating a user is present at the surgeon console. Next, at or right after time $t_1$, the first decision change occurs and user-presence/absence classifier begins outputting user-absence decisions (0), indicating the user has left the surgeon console at around time $t_1$. From time $t_1$ onward, user-presence/absence classifier continues outputting user-absence decisions (0) until time $t_2$, at which time the second decision change occurs and user-presence/absence classifier begins outputting user-presence decisions (1). As described above, a transition from user-absence decisions to user-presence decisions can indicate that a user has returned to the surgeon console. In some embodiments, the user-switching detection mechanism detects such a transition in surgical workflow 800, and subsequently generates a dialog window/box on the monitor of the surgeon console promoting the user to confirm herself/himself as either the same user or a new user. In some embodiments, to avoid false positives, the disclosed user-switching detection mechanism only generates the dialog window/box if a minimum number (e.g., 10) of consecutive user-presence decisions (1) have been generated after time $t_2$. In surgical workflow 800, a dialog window/box 806 including a question "Are you the same surgeon?" was generated by user-switching detection mechanism at some time after time $t_2$.

From time $t_2$ in surgical workflow 800, user-presence/absence classifier only outputs user-presence decisions (1) for a brief time interval between $t_2$ to $t_3$. This short time interval is immediately followed by the third decision change at time $t_3$, after which time user-presence/absence classifier begins outputting user-absence decisions (0). Note that this short time interval ($t_2$, $t_3$) can be the result of a user enters the user seating area but only for a very brief moment, and subsequently leaves the user seating area. As a result, the user may not respond to dialog window/box 806 during the short time interval ($t_2$, $t_3$).

From time $t_3$ onward, user-presence/absence classifier continues outputting user-absence decisions (0) until time $t_4$, at which time the fourth decision change occurs and user-presence/absence classifier again begins outputting user-presence decisions (1). However, as surgical workflow 800 shows, this new user-presence decision period is extremely short and ends at time is almost immediately after it begins at time $t_4$. In this scenario, the disclosed user-switching detection mechanism does not generate a new dialog window/box because the previously generated dialog window/box 806 has not been answered and therefore remains valid. Note that the user-switching detection mechanism may not generate a dialog window/box even if dialog window/box 806 does not exist for the reason that the time interval ($t_4$, $t_5$) may contain fewer than the minimum number (e.g., 10) of consecutive user-presence decisions (1) required to avoid false positives.

From time $t_5$ onward, user-presence/absence classifier continues outputting user-absence decisions (0) until time $t_6$, at which time the fifth decision change occurs and user-presence/absence classifier again begins outputting user-presence decisions (1). From time $t_6$ onward, user-presence/absence classifier continues outputting user-presence decisions (1) for a prolonged time period indicating a user continues to be present at the surgeon console. Moreover, the returned user may now respond to dialog window/box 806 with a "Yes" answer, confirming that he/she is the same user as the previous user at the user seating area before time $t_1$. Note that dialog window/box 806 generated around time $t_2$ remains valid at time $t_6$ because it has not been responded, so that the disclosed user-switching detection mechanism does not need to generate another dialog window/box around time $t_6$ for the returned user.

Figure 9:
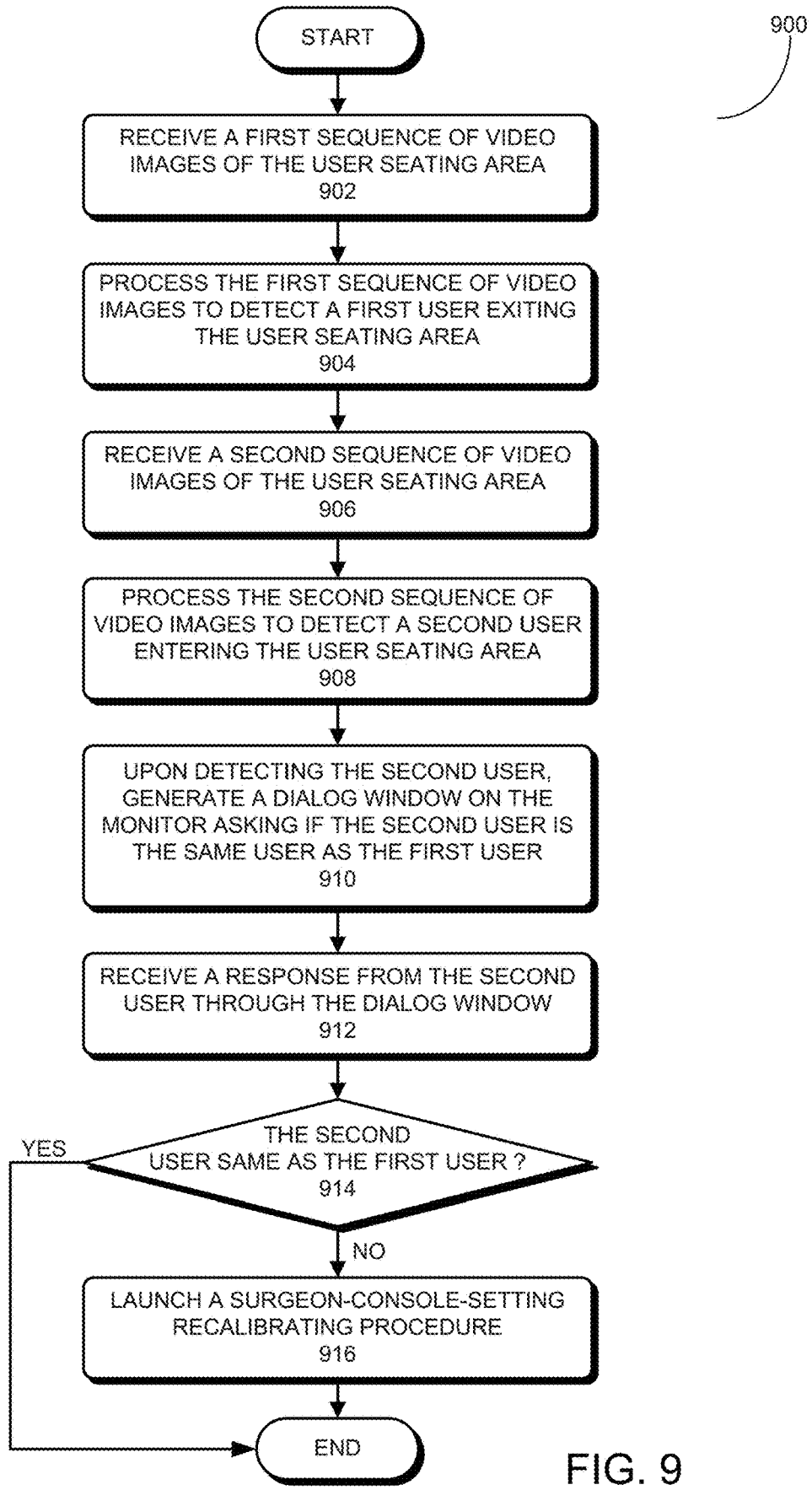
FIG. 9 presents a flowchart illustrating an exemplary process for tracking users at a surgeon console during a surgical session using a trained user-presence/absence classifier in accordance with some embodiments described herein.

FIG. 9 presents a flowchart illustrating an exemplary process 900 for tracking users at a surgeon console during a surgical session using a trained user-presence/absence classifier in accordance with some embodiments described herein. In one or more embodiments, one or more of the steps in FIG. 9 may be omitted, repeated, and/or performed in a different order. Accordingly, the specific arrangement of steps shown in FIG. 9 should not be construed as limiting the scope of the technique.

Process 900 may begin by receiving a first sequence of video images of the user seating area of the surgeon console (step 902). Process 900 subsequently processes the first sequence of video images to detect an event that a first user in the user seating area exiting the user seating area (step 904). To detect the event that the first user is exiting the user seating area, process 900 can generate a sequence of user-presence/absence decisions corresponding to the first sequence of video images using the disclosed user-presence/absence image classifier, such as the trained user-presence/absence classifier 310, and detect a transition that the decision outputs change from user-presence decisions (1) to user-absence decisions (0). Process 900 next receives a second sequence of video images of the user seating area (step 906). Process 900 subsequently processes the second sequence of video images to detect an event that a second user entering the user seating area (step 908). To detect the event that the second user entering the user seating area, process 900 can generate a sequence of user-presence/absence decisions corresponding to the second sequence of video images using the disclosed user-presence/absence image classifier, and detect a transition that the decision outputs change from user-absence decisions (0) to user-presence decisions (1).

Upon detecting the second user entering the user seating area, process 900 subsequently generates a dialog window on the monitor of the surgeon console asking the second user to confirm whether he/she is the same user as the first user (step 910). In some embodiments, process 900 generates the dialog window only after a minimum number of consecutive user-presence decisions (1) have been generated by the user-presence/absence classifier following the user-absence decisions (0) in order to avoid false positives.

Process 900 next receives a response from the second user through the dialog window (step 912) and determines if the second user is the same user as the first user based on the response (step 914). If so, process 900 determines that surgeon console settings do not need to be recalibrated or reconfigured and process 900 terminates. However, if the second user is not the same user as the first user, i.e., the second user being a new user, process 900 determines that surgeon console settings needs to be recalibrated or reconfigured and subsequently launches a surgeon-console-setting recalibrating procedure (step 916). For example, process 900 can simply generate another dialog window prompting the user to enter his/her identify, which causes robotic surgical system 100 to load new surgeon-console-settings, such as user gaze-tracking settings, user UID-control settings, and user seat settings for the second user.

Figure 10:
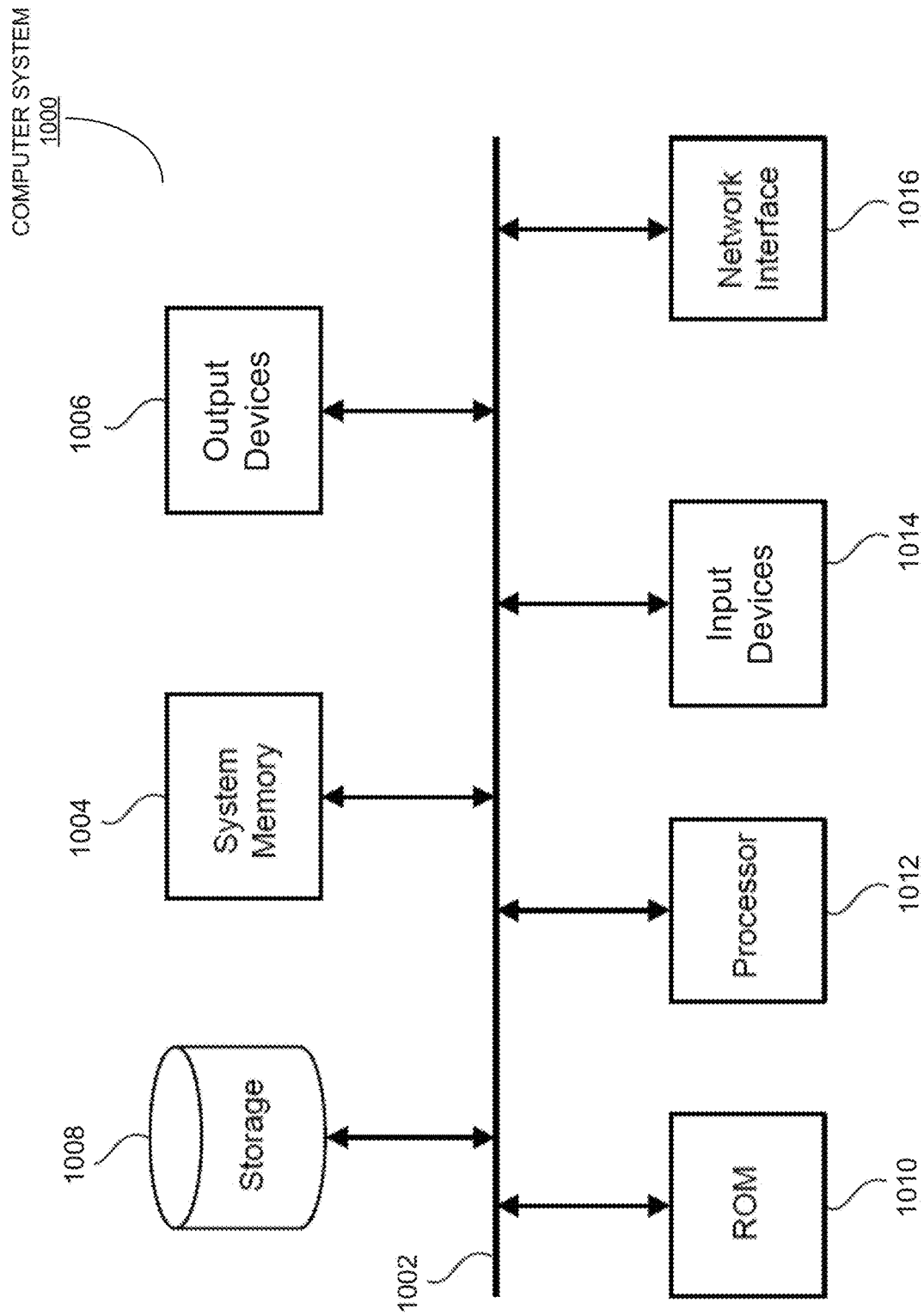
FIG. 10 conceptually illustrates a computer system with which some embodiments of the subject technology can be implemented.

FIG. 10 conceptually illustrates a computer system with which some embodiments of the subject technology can be implemented. Computer system 1000 can be a client, a server, a computer, a smartphone, a PDA, a laptop, or a tablet computer with one or more processors embedded therein or coupled thereto, or any other sort of computing device. Such a computer system includes various types of computer-readable media and interfaces for various other types of computer-readable media. Computer system 1000 includes a bus 1002, processing unit(s) 1012, a system memory 1004, a read-only memory (ROM) 1010, a permanent storage device 1008, an input device interface 1014, an output device interface 1006, and a network interface 1016. In some embodiments, computer system 1000 is a part of a robotic surgical system.

Bus 1002 collectively represents all system, peripheral, and chipset buses that communicatively connect the numerous internal devices of computer system 1000. For instance, bus 1002 communicatively connects processing unit(s) 1012 with ROM 1010, system memory 1004, and permanent storage device 1008.

From these various memory units, processing unit(s) 1012 retrieves instructions to execute and data to process in order to execute various processes described in this patent disclosure, including the above-described techniques for building a CNN-based user-presence/absence classifier and for tracking users at a surgeon console during a surgical session using the disclosed user-presence/absence classifier described in conjunction with FIGS. 3-9. The processing unit(s) 1012 can include any type of processor, including, but not limited to, a microprocessor, a graphic processing unit (GPU), a tensor processing unit (TPU), an intelligent processor unit (IPU), a digital signal processor (DSP), a field-programmable gate array (FPGA), and an application-specific integrated circuit (ASIC). Processing unit(s) 1012 can be a single processor or a multi-core processor in different implementations.

ROM 1010 stores static data and instructions that are needed by processing unit(s) 1012 and other modules of the computer system. Permanent storage device 1008, on the other hand, is a read-and-write memory device. This device is a non-volatile memory unit that stores instructions and data even when computer system 1000 is off. Some implementations of the subject disclosure use a mass-storage device (such as a magnetic or optical disk and its corresponding disk drive) as permanent storage device 1008.

Other implementations use a removable storage device (such as a floppy disk, flash drive, and its corresponding disk drive) as permanent storage device 1008. Like permanent storage device 1008, system memory 1004 is a read-and-write memory device. However, unlike storage device 1008, system memory 1004 is a volatile read-and-write memory, such as a random access memory. System memory 1004 stores some of the instructions and data that the processor needs at runtime. In some implementations, various processes described in this patent disclosure, including the above-described techniques for building a CNN-based user-presence/absence classifier and for tracking users at a surgeon console during a surgical session using the disclosed user-presence/absence classifier described in conjunction with FIGS. 3-9, are stored in system memory 1004, permanent storage device 1008, and/or ROM 1010. From these various memory units, processing unit(s) 1012 retrieves instructions to execute and data to process in order to execute the processes of some implementations.

Bus 1002 also connects to input and output device interfaces 1014 and 1006. Input device interface 1014 enables the user to communicate information and select commands for the computer system. Input devices used with input device interface 1014 include, for example, alphanumeric keyboards and pointing devices (also called "cursor control devices"). Output device interface 1006 enables, for example, the display of images generated by the computer system 1000. Output devices used with output device interface 1006 include, for example, printers and display devices, such as cathode ray tubes (CRT) or liquid crystal displays (LCD). Some implementations include devices such as a touchscreen that functions as both input and output devices.

Finally, as shown in FIG. 10, bus 1002 also couples computer system 1000 to a network (not shown) through a network interface 1016. In this manner, the computer can be a part of a network of computers (such as a local area network ("LAN"), a wide area network ("WAN"), an intranet, or a network of networks, such as the Internet. Any or all components of computer system 1000 can be used in conjunction with the subject disclosure.

The various illustrative logical blocks, modules, circuits, and algorithm steps described in connection with the embodiments disclosed in this patent disclosure may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

The hardware used to implement the various illustrative logics, logical blocks, modules, and circuits described in connection with the aspects disclosed herein may be implemented or performed with a general purpose processor, a digital signal processor (DSP), an application-specific integrated circuit (ASIC), a field-programmable gate array (FPGA) or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of receiver devices, e.g., a combination of a DSP and a microprocessor, a plurality of microprocessors, one or more microprocessors in conjunction with a DSP core, or any other such configuration. Alternatively, some steps or methods may be performed by circuitry that is specific to a given function.

In one or more exemplary aspects, the functions described may be implemented in hardware, software, firmware, or any combination thereof. If implemented in software, the functions may be stored as one or more instructions or code on a non-transitory computer-readable storage medium or non-transitory processor-readable storage medium. The steps of a method or algorithm disclosed herein may be embodied in processor-executable instructions that may reside on a non-transitory computer-readable or processor-readable storage medium. Non-transitory computer-readable or processor-readable storage media may be any storage media that may be accessed by a computer or a processor. By way of example but not limitation, such non-transitory computer-readable or processor-readable storage media may include RAM, ROM, EEPROM, flash memory, CD-ROM or other optical disk storage, magnetic disk storage or other magnetic storage devices, or any other medium that may be used to store desired program code in the form of instructions or data structures and that may be accessed by a computer. Disk and disc, as used herein, includes compact disc (CD), laser disc, optical disc, digital versatile disc (DVD), floppy disk, and Blu-ray disc where disks usually reproduce data magnetically, while discs reproduce data optically with lasers. Combinations of the above are also included within the scope of non-transitory computer-readable and processor-readable media. Additionally, the operations of a method or algorithm may reside as one or any combination or set of codes and/or instructions on a non-transitory processor-readable storage medium and/or computer-readable storage medium, which may be incorporated into a computer-program product.

While this patent document contains many specifics, these should not be construed as limitations on the scope of any disclosed technology or of what may be claimed, but rather as descriptions of features that may be specific to particular embodiments of particular techniques. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described, and other implementations, enhancements and variations can be made based on what is described and illustrated in this patent document.

What is claimed is:

1. A computer-implemented method for detecting user switching events at a surgeon console in a robotic surgical system, the method comprising:
    receiving a first sequence of video images capturing a user seating area of the surgeon console;
    processing, using a user-presence/absence classifier, the first sequence of video images to detect a first user exiting the user seating area after detecting the first user being present at the user seating area;
    receiving a second sequence of video images capturing the user seating area;
    processing, using the user-presence/absence classifier, the second sequence of video images to detect a second user entering the user seating area;
    generating a window on a monitor of the surgeon console prompting the second user to respond whether the second user is the same user as the first user, wherein the window is generated after a minimum time threshold of detecting the second user at the user seating area following a detecting of a user absence at the user seating area based on the processing of the second sequence of video images, thereby avoiding false positives;
    receiving a response from the second user;
    determining whether the second user is the same as the first user based on the received response; and
    determining that a user switching event has occurred at the surgeon console in response to determining that the second user is not the same as the first user.

2. The computer-implemented method of claim 1, wherein processing, using the user-presence/absence classifier, the first sequence of video images to detect the first user exiting the user seating area includes:
    applying the user-presence/absence classifier to the first sequence of video images to generate a corresponding sequence of user-presence/user-absence classifications, wherein the user-presence/absence classifier is configured to output a binary classification for each input image as either a user-presence classification or a user-absence classification; and
    detecting the first user exiting the user seating area when the generated user-presence/user-absence classifications transition from continuous user-presence classifications to user-absence classifications.

3. The computer-implemented method of claim 2, wherein processing, using the user-presence/absence classifier, the second sequence of video images to detect the second user entering the user seating area includes:
    applying the user-presence/absence classifier to the second sequence of video images to generate a corresponding sequence of user-presence/user-absence classifications; and
    detecting the second user entering the user seating area when the generated user-presence/user-absence classifications transition from continuous user-absence classifications to user-presence classifications.

4. The computer-implemented method of claim 2, wherein the user-presence/absence classifier includes a neural network model that further comprises a stack of feature-extraction layers having a first set of parameters, which is followed by a fully-connected layer having a second set of parameters, which is further followed by a final output layer that outputs the user-presence/user-absence classifications.

5. The computer-implemented method of claim 4, wherein prior to detecting the user switching event, the method further comprises training the user-presence/absence classifier by:
    receiving a set of training images of the user seating area, wherein each training image in the set of training images is either labeled with a user-presence label or a user-absence label;
    for each labeled training image in the set of training images, using the stack of feature-extraction layers of the neural network model to extract a set of two-dimensional (2D) feature maps of the labeled training image while freezing the first set of parameters;
    training the second set of parameters of the fully-connected layer of the neural network model based at least on the set of extracted 2D feature maps extracted from the set of training images and corresponding user-presence/user-absence labels to obtain a trained fully-connected layer; and
    freezing both the first set of parameters and the trained second set of parameters in the neural network model to obtain the trained user-presence/absence classifier.

6. The computer-implemented method of claim 4, wherein the final output layer includes a binary Softmax layer.

7. The computer-implemented method of claim 1, wherein the response from the second user is received through the window.

8. The computer-implemented method of claim 1, wherein the window is generated after a minimum number of consecutive user-presence classifications have been generated following a set of consecutive user-absence classifications by applying the user-presence/absence classifier to the second sequence of video images.

9. The computer-implemented method of claim 1, wherein after determining that a user switching event has occurred, the method further comprises:
 determining an identity of the second user; and
 launching a surgeon-console recalibration procedure to recalibrate a set of settings of the surgeon console for the identified second user.

10. The computer-implemented method of claim 9, wherein the set of settings of the surgeon console includes one or more of:
 user gaze-tracking settings;
 user interface device (UID)-control settings; and
 user seat settings.

11. The computer-implemented method of claim 9, wherein in response to determining that the second user is the same as the first user, the method comprises maintaining the set of settings of the surgeon console for the first user.

12. An apparatus, comprising:
 one or more processors; and
 a memory coupled to the one or more processors, wherein the memory stores instructions that, when executed by the one or more processors, cause the apparatus to:
  receive a first sequence of video images capturing a user seating area of a surgeon console;
  process, using a user-presence/absence classifier, the first sequence of video images to detect a first user exiting the user seating area after detecting the first user being present at the user seating area;
  receive a second sequence of video images capturing the user seating area;
  process, using the user-presence/absence classifier, the second sequence of video images to detect a second user entering the user seating area;
  generate a window on a monitor of the surgeon console prompting the second user to respond whether the second user is the same user as the first user, wherein the window is generated after a minimum time threshold of detecting the second user at the user seating area following a detecting of a user absence at the user seating area based on the processing of the second sequence of video images, thereby avoiding false positives;
  receive a response from the second user;
  determine whether the second user is the same as the first user based on the received response; and
  determine that a user switching event has occurred at the surgeon console in response to determining that the second user is not the same as the first user.

13. The apparatus of claim 12, wherein the memory further stores instructions that, when executed by the one or more processors, cause the apparatus to process, using the user-presence/absence classifier, the first sequence of video images to detect the first user exiting the user seating area by:
 applying the user-presence/absence classifier to the first sequence of video images to generate a corresponding sequence of user-presence/user-absence classifications, wherein the user-presence/absence classifier is configured to output a binary classification for each input image as either a user-presence classification or a user-absence classification; and
 detecting the first user exiting the user seating area when the generated user-presence/user-absence classifications transition from continuous user-presence classifications to user-absence classifications.

14. The apparatus of claim 13, wherein the memory further stores instructions that, when executed by the one or more processors, cause the apparatus to process, using the user-presence/absence classifier, the second sequence of video images to detect the second user entering the user seating area by:
 applying the user-presence/absence classifier to the second sequence of video images to generate a corresponding sequence of user-presence/user-absence classifications; and
 detecting the second user entering the user seating area when the generated user-presence/user-absence classifications transition from continuous user-absence classifications to user-presence classifications.

15. The apparatus of claim 12, wherein
the response from the second user is received through the window.

16. The apparatus of claim 12, wherein after determining that a user switching event has occurred, the memory further stores instructions that, when executed by the one or more processors, cause the apparatus to:
 determine an identity of the second user; and
 launch a surgeon-console recalibration procedure to recalibrate a set of settings of the surgeon console for the identified second user, wherein the set of settings includes one or more of:
 user gaze-tracking settings;
 user interface device (UID)-control settings; and
 user seat settings.

17. A robotic surgical system, comprising:
 a surgeon console including a user seating area and a display device; and
 a computer at the surgeon console configured to detect a user switching event at the surgeon console by:
  receiving a first sequence of video images capturing a user seating area of the surgeon console;
  processing, using a user-presence/absence classifier, the first sequence of video images to detect a first user exiting the user seating area after detecting the first user being present at the user seating area;
  receiving a second sequence of video images capturing the user seating area;
  processing, using the user-presence/absence classifier, the second sequence of video images to detect a second user entering the user seating area;
  generating a window on a monitor of the surgeon console prompting the second user to respond whether the second user is the same user as the first user, wherein the window is generated after a minimum time threshold of detecting the second user at the user seating area following a detecting of a user absence at the user seating area based on the processing of the second sequence of video images, thereby avoiding false positives;
  receiving a response from the second user;
  determining whether the second user is the same as the first user based on the received response; and
  determining that a user switching event has occurred at the surgeon console in response to determining that the second user is not the same as the first user.

18. The robotic surgical system of claim 17, wherein the computer is configured to process, using the user-presence/absence classifier, the first sequence of video images by:
- applying the user-presence/absence classifier to the first sequence of video images to generate a corresponding sequence of user-presence/user-absence classifications, wherein the user-presence/absence classifier is configured to output a binary classification for each input image as either a user-presence classification or a user-absence classification; and
- detecting the first user exiting the user seating area when the generated user-presence/user-absence classifications transition from continuous user-presence classifications to user-absence classifications.

19. The robotic surgical system of claim 18, wherein the computer is configured to process, using the user-presence/absence classifier, the second sequence of video images by:
- applying the user-presence/absence classifier to the second sequence of video images to generate a corresponding sequence of user-presence/user-absence classifications; and
- detecting the second user entering the user seating area when the generated user-presence/user-absence classifications transition from continuous user-absence classifications to user-presence classifications.

20. The robotic surgical system of claim 17, wherein the response from the second user is received through the window.

* * * * *